US008916197B2

(12) United States Patent
Sou et al.

(10) Patent No.: US 8,916,197 B2
(45) Date of Patent: Dec. 23, 2014

(54) BONE MARROW-DIRECTING DRUG DELIVERY MATERIALS AND THEIR APPLICATIONS

(75) Inventors: Keitaro Sou, Tokyo (JP); Shinji Takeoka, Tokyo (JP); Eishun Tsuchida, Tokyo (JP); Beth A. Goins, San Antonio, TX (US); William T. Phillips, San Antonio, TX (US)

(73) Assignees: The Board of Regents of the University of Texas System, Austin, TX (US); Waseda University, Shinjuku-Ku (JP)

( * ) Notice: Subject to any disclaimer, the term of this patent is extended or adjusted under 35 U.S.C. 154(b) by 1735 days.

(21) Appl. No.: 11/916,648

(22) PCT Filed: Jun. 5, 2006

(86) PCT No.: PCT/JP2006/311676
§ 371 (c)(1),
(2), (4) Date: Jun. 29, 2009

(87) PCT Pub. No.: WO2006/132388
PCT Pub. Date: Dec. 14, 2006

(65) Prior Publication Data
US 2009/0297608 A1 Dec. 3, 2009

(30) Foreign Application Priority Data
Jun. 6, 2005 (JP) ................. 2005-165763

(51) Int. Cl.
*A61K 9/00* (2006.01)
*A61K 9/14* (2006.01)
*A61K 9/127* (2006.01)
*A61K 51/12* (2006.01)

(52) U.S. Cl.
CPC ............ *A61K 9/0019* (2013.01); *A61K 9/1271* (2013.01); *A61K 51/1227* (2013.01); *Y10S 977/906* (2013.01)
USPC ............................ 424/489; 424/400; 977/906

(58) Field of Classification Search
None
See application file for complete search history.

(56) References Cited

U.S. PATENT DOCUMENTS

| 5,370,877 | A * | 12/1994 | Rosenberg et al. | 424/450 |
| 6,610,322 | B1 * | 8/2003 | Keller et al. | 424/450 |
| 6,965,049 | B2 * | 11/2005 | Tsuchida et al. | 560/170 |
| 2003/0026831 | A1 | 2/2003 | Lakkaraju et al. | 424/450 |
| 2004/0028638 | A1 | 2/2004 | Tsuchida et al. | 424/70.22 |

FOREIGN PATENT DOCUMENTS

| EP | 1 420 010 | 5/2004 |
| JP | 1994-080560 | 3/1994 |
| JP | 2002-205959 | 7/2002 |
| JP | 2003-064037 | 3/2003 |
| JP | 2003-520713 | 7/2003 |
| JP | 2004-203862 | 7/2004 |
| WO | WO 01/16211 | 3/2001 |
| WO | WO 01/56548 | 8/2001 |
| WO | WO 01/82973 | 11/2001 |
| WO | WO 02/38530 | 5/2002 |
| WO | WO 03/015753 | 2/2003 |
| WO | WO 03/018539 | 3/2003 |
| WO | WO 03018539 A1 * | 3/2003 |
| WO | WO 03/103822 | 12/2003 |
| WO | WO 2004/089345 | 10/2004 |

OTHER PUBLICATIONS

Moghimi, S.M., "Modulation of lymphatic distribution of subcutaneously injected poloxamer 407-coated nanospheres: the effect of the ethylene oxide chain configuration", 2003, FEBS LEtters, pp. 241-244.*
Arulsudar et al., "Preparation, characterization and biodistribution of (99m)tc-labeled liposome encapsulated cyclosporine," *Journal of Drug Targeting*, 11:187-196, 2003.
Awashthi et al., "Neutral and anionice liposome-encapsulated hemoglobin: effect of postinserted poly(ethylene glycol)-distearoylphosphatidylethanolamine on distribution and circulation kinetics," *Journal of Pharmacology and Experimental Therapeutics*, 309:241-248, 2004.
Dietz, "Distribution of bone marrow, bone, and bone-ash in rabbits," *Proc.Soc. Exp. Med.*, 57:60-62, 1944.
International Preliminary Report and Written Opinion, issued in International Application No. PCT/JP2006/311676, dated Dec. 21, 2007.
Kaplan and Timmons, "The Rabbit: a model for the principles of mammalian physiology and surgery," Academic Press, New York, 1979.
Kozma et al., Anatomy, physiology, and biochemistry of the rabbit, in the Biology of the Laboratory Rabbit, in *The Biology of the Laboratory Rabbit*, Chapter 3, eds. Weisbroth et al., New York: Academic Press, 50-72, 1974.
Lefevre et al., "Texas Res-X and rhodamine Red-X, new derivatives of sulforhodamine 101 and lissamine rhodamine B with improved labeling and fluorescence properties," *Bioconjug. Chem.*, 7:482-489, 1996.
Levine et al., "Cardiopulmonary toxicity after liposomal amphotericin B infusion," *Ann. Intern. Med.*, 114:664-666, 1991.
Pierigè et al., "Cell-based drug delivery," *Advanced Drug Delivery Reviews*, 60:286-295, 2008.
Reinish et al., "Interactions of liposomes and platelets ," *Throm. Haemost.*, 60:518-523, 1988.
Senior et al., "Tissue distribution of liposomes exhibiting long half-lives in the circulation after intravenous injection," *Biochimica et Biophysica Acta*, 839:1-8, 1985.
Sou et al., "Effective encapsulation of proteins into size-controlled phospholipid vesicles using freeze-thawing and extrusion," *Biotechnol. Prog.*, 19:1547-1552, 2003.

(Continued)

*Primary Examiner* — Michael G Hartley
*Assistant Examiner* — Lance Rider
(74) *Attorney, Agent, or Firm* — Fulbright & Jaworski LLP

(57) ABSTRACT

The present invention pertains to a bone marrow-directing drug delivery material that includes at least one fine particle, wherein the fine particle includes an anionic moiety on a surface of the particle. Also disclosed are uses of the material set forth herein for the prevention, treatment, or diagnosis of a disease of bone, cartilage, bone marrow, or a joint. Also disclosed are methods of preventing, treating, or diagnosing a disease of bone, cartilage, bone marrow, or a joint in a subject, involving administering to the subject a pharmaceutically effective amount of the material of the present invention.

12 Claims, 5 Drawing Sheets

(56) References Cited

OTHER PUBLICATIONS

Sou et al., "Loading of curcumin into macrophages using lipid-based nanoparticles," *International Journal of Pharmaceutics*, 352:287-293, 2008.

Sou et al., "Poly(ethylene glycol)-modification of the phospholipid vesicles by using the spontaneous incorporation of poly(ethylene glycol)-lipid into the vesicles," *Bioconjug. Chem.*, 11:372-379, 2000.

Wassana et al., "Efficient targeting to alveolar macrophages by intratracheal administration of mannosylated liposomes in rats," *Journal of Controlled Release*, 125:121-130, 2008.

Woodle and Lasic, "Sterically stabilized liposomes," *Biochem. Biophys. Acta*, 1113:171-199, 1992.

International Search Report and Written Opinion issued in PCT Application No. PCT/JP2006/311676, mailed Oct. 22, 2012.

Office Communication, issued in Japanese Patent Application 2008-514359, mailed on Apr. 3, 2012. (English Translation).

* cited by examiner

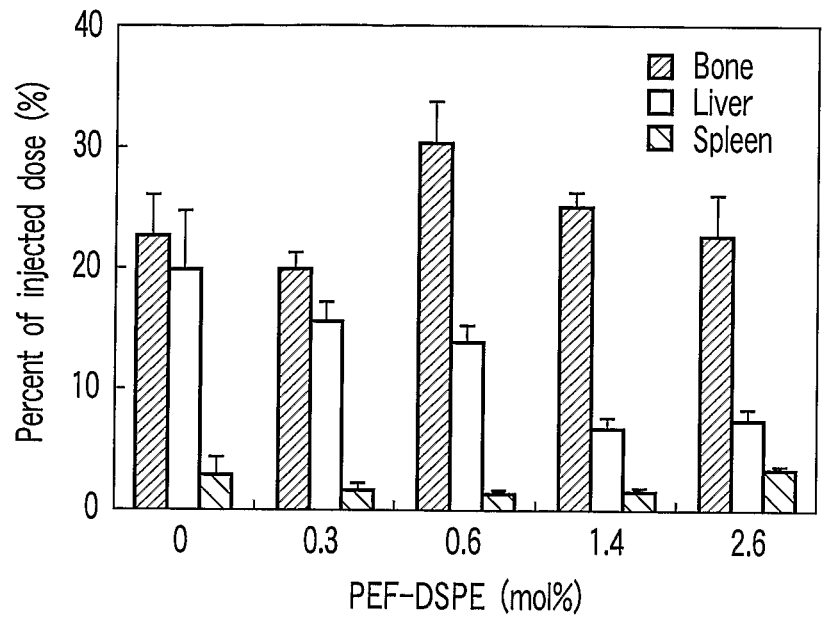
F I G. 3
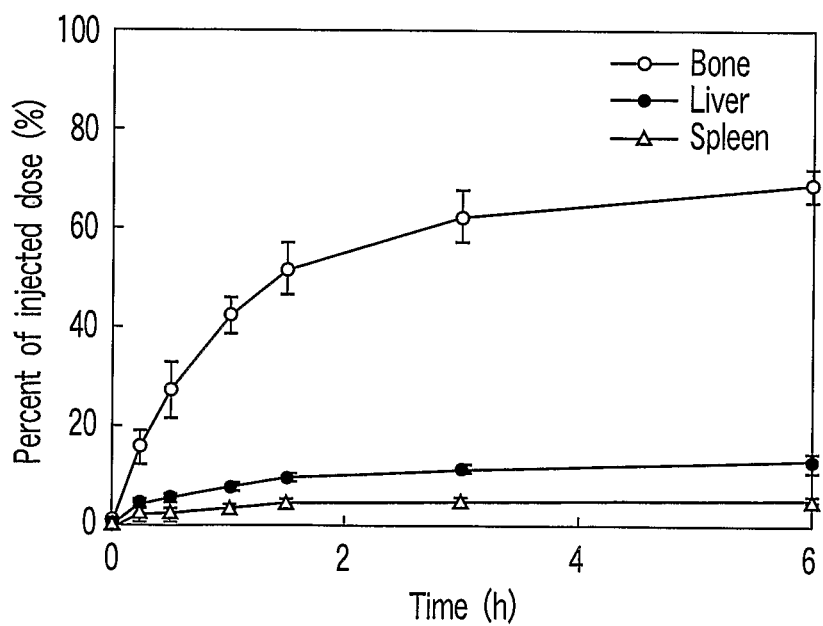
F I G. 5

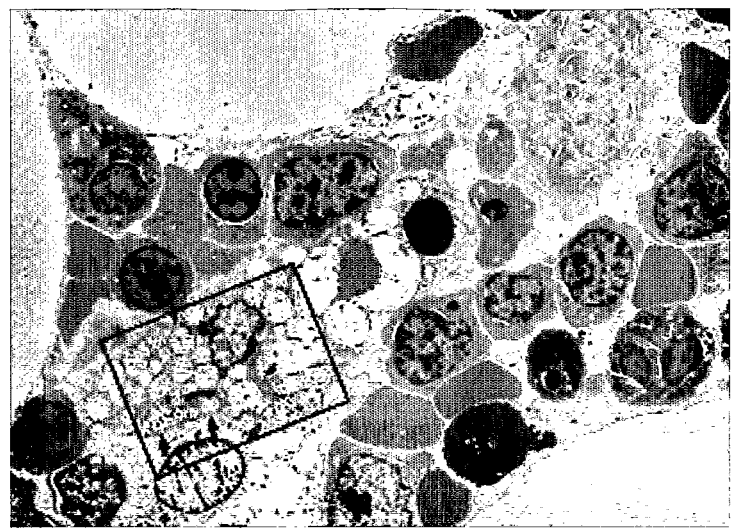
5.0μm
F I G. 7A
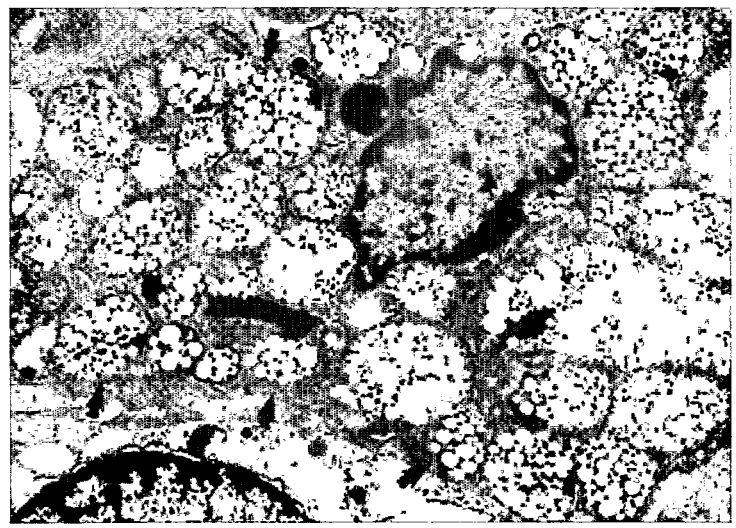
0.5μm
F I G. 7B

BONE MARROW-DIRECTING DRUG DELIVERY MATERIALS AND THEIR APPLICATIONS

This application is a national phase application under 35 U.S.C. §371 of International Application No. PCT/JP2006/311676 filed Jun. 5, 2006, which claims priority to Japanese Patent application No. 2005-165763, filed Jun. 6, 2005. The entire contents of each of the above-referenced disclosures is hereby specifically incorporated by reference.

TECHNICAL FIELD

The present invention relates to the fields of pharmaceutical sciences and clinical medicine. More particularly, the present invention relates to drug delivery materials which may be used in various applications, such as the diagnosis, treatment or prevention of diseases of bone, bone marrow, cartilage, and joints.

BACKGROUND ART

The intravenous administration of a drug comprised in the form of a solution to treat a site of disease that is distal from the site of injection is common. However, following intravenous administration, the drug spreads throughout the whole body of the subject, and most is excreted, such as through the urine. Thus, a patient may need a relatively large dose of the drug to allow for therapeutic levels at the site of disease. In many cases it may not be possible to administer the required therapeutic dose because an excessively large dose may result in side effects of the drug or uncertainty regarding the safety of a drug. Thus, there is the need for novel methods and materials for delivering therapeutic agents more efficiently to sites of disease with reduction in the risk of side effects.

Colloidal particles (size: 0.02-5 μm as diameter) have been described as drug delivery materials. However, for the most part, they become trapped within the reticuloendothelial system of the liver and spleen when administered to mammals. This has been a major obstacle of efficient drug delivery.

Vesicles have been described as delivery materials which can carry various materials within their inner aqueous phases or bi-layer membranes. However, they are rapidly removed from the blood by becoming trapped within the reticuloendothelial system of the liver and spleen. Accordingly, studies have been performed to extend the residence time of vesicles within blood by adjusting the composition or diameter of the vesicles, or modifying the surface of the vesicles. As a result, it has been reported that the surface modification of vesicles by polyethylene glycol (PEG) chain is effective in reducing the trapping within the reticuloendothelial system of the liver and spleen, and to prolong the residence time of vesicles within blood.

It has been reported that prolonged residency of PEG-vesicles in the blood passively improved the amount of drug delivery to a metabolically active site (for example, tumor), even if it did not use a special accumulation mechanism. This means that the trapping of the intravenously injected vesicles into living tissues is a competitive process. This is known as passive drug delivery, because the uptake into internal organs and tissues of interest is increased by the slower trapping rate of the reticuloendothelial system of the liver and spleen. Passive drug delivery lacks site-directed specificity, and consequently, there is inefficient delivery to specific sites of disease.

Thus, there has been strong interest in the identification of methods to actively direct therapeutic agents to specific sites of disease in a subject. For example, it has been found that cationic vesicles can be utilized to introduce genes into cells. In this regard, various types of cationic vesicles have been proposed, and the possibility of their application in gene therapy is under evaluation. Although the vesicles containing cationic lipids have been demonstrated to accumulate in a targeted site in a simplified model system such as cultured cells, such an effect has not been confirmed in vivo. Although the surface of some active drug delivering materials sometimes shows physiologic activity, the trapping into reticuloendothelial system of the liver and spleen has been an obstacle in vivo.

It has been known that anionic phospholipids (e.g., phosphatidylglycerol, phosphatidylserine and phosphatidylinositol), which have been utilized in anionic vesicles, induce activation of complement or thrombocytopenia (see Reinish et al., Throm. Haemost., 60(3):518-523, 1988; Levine et al., Ann. Intern. Med., 114(8):664-666, 1991). The anionic vesicles sensitized by this immunoreaction are immediately trapped by the phagocytes of the liver or spleen, and can hardly reach bones.

Meanwhile, negatively charged molecules such as phosphoric acid compounds are known to exhibit bone-affinity. This is due to the interaction of these molecules with the positive charge of calcium ions, which exists in the hydroxyapatite of the bone tissues, following intravascular administration. For example, phosphoric acid compounds carrying radioactive labels are utilized in bone scintigraphy. On the other hand, anionic vesicle systems having phosphoric acid residues as charged groups are for the most part removed due to trapping within the reticuloendothelial system of the liver and spleen, and their bone marrow directing property has not been reported. For example, JP-A-2004-203862 discloses vesicles containing phospholipids modified with silyl groups having hydroxyl groups that have affinity to bones. However, no working Examples which demonstrate that the vesicles actually accumulated in bone were set forth.

The bone marrow plays an important role as a hematopoietic organ, and bone diseases such as osteomyelitis and myeloma cause severe morbidity. Since the bone marrow is not an organ to which surgical therapy is an option, the bone marrow diseases are mainly subject to medical treatment, such as by chemotherapy. Further, the bone marrow is highly sensitive to drugs and radiation, and damage to the bone marrow often causes severe side effects. Therefore, there is a great need for drug delivery systems that have the ability to effectively deliver therapeutic agents to the bones or bone marrow. These agents could be bone marrow protecting agents to specifically protect against the toxic effects of chemotherapy or radiotherapy. Bone-targeted agents could also be used as safe and efficient diagnostic agents for the diagnosis of diseases of bone or bone marrow. Presently, there are no effective means for efficiently delivering drugs to the bone marrow. Administration of therapeutic agents to bone marrow using current technology has frequently resulted in unwanted side effects, presenting an obstacle to the therapeutic treatment. Thus, there is the need for more effective methods of targeting therapeutic agents to the bone marrow with minimal side effects.

DISCLOSURE OF THE INVENTION

The present inventors have identified novel drug delivery materials that have the ability to target therapeutic agents to the bones with high specificity. These agents also have the ability to result in accumulation of therapeutic agents in bones.

In particular, the inventors have found that a physiologically inactive anionic group, i.e., an anionic group, other than a physiologically active phosphoric acid residue conventionally used in the art, when carried on the surface of a drug delivery material, has the ability to specifically target therapeutic agents to the bones or bone marrow. Taking vesicles carrying carboxylic acid residues as an example, the present inventors have demonstrated that such vesicles exhibit high affinity for the bone marrow. This is based on the fact that such vesicles were intravenously administered to a living body and the distribution of the vesicles in the organs in the body was quantitatively analyzed, thus finding that such vesicles can be utilized as a drug delivery material to the bone marrow. Further, the present inventors have succeeded in efficiently accumulating delivery material in the bone marrow with the uptake in the liver being suppressed, by modifying the surface of the delivery material with an appropriate amount of a polyethylene glycol (PEG) which does not shield the effects of the anionic group on the surface of the delivery material.

The present invention is generally directed to bone marrow directing drug delivery materials that include at least one fine particle that includes an anionic moiety on the surface of the particle. In some embodiments, the fine particle has a diameter of about 0.01 nm to 5 μm in diameter. In particular embodiments the fine particle has a diameter of 0.02 μm to 1 μm.

In particular embodiments, the material is composed of a plurality of fine particles. The particles can be of a single diameter, or can vary in diameter. In preferred embodiments, the fine particles have an average diameter of 0.02 μm to 1 μm.

The fine particle can be of any structure or composition. In particular embodiments, the fine particle is further defined as including an aggregate of molecules of at least one amphipathic compound. For example, the amphipathic compound may include an anionic group in the hydrophilic portion of the amphipathic compound.

The fine particle may or may not be a solid particle. In some embodiments, the fine particle is composed of an aggregate of molecules that forms a vesicle.

The anionic moiety is defined herein to refer to a part of the molecule that carries a negative charge. For example, the anionic moiety may be a carboxylic acid group.

The amphipathic compound can be any amphipathic compound known to those of ordinary skill in the art. In some embodiments, the amphipathic compound is a fatty acid or a salt thereof. For example, the amphipathic compound may be a compound represented by formula (1):

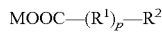

MOOC—(R$^1$)$_p$—R$^2$ where M is a hydrogen atom or a monovalent cation, R$^1$ is a spacer, R$^2$ is a hydrophobic group, and p is 0 or 1. Alternatively, the amphipathic compound is represented by formula (2):

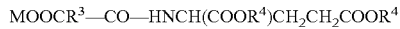

MOOCR$^3$—CO—HNCH(COOR$^4$)CH$_2$CH$_2$COOR$^4$ where M is a hydrogen atom or a monovalent cation, R$^3$ represents -CH$_2$CH$_2$— or —CH(CH$_3$)CH$_2$—, and R$^4$ represents a C$_{12}$-C$_{22}$ alkyl group.

The fine particle may or may not be further defined as including a water soluble polymer. For example, the water soluble polymer may be bound to a surface of the fine particle. The material may, for example, include a mixture of fine particles, wherein some of the fine particles include a water soluble polymer. In further embodiments, all of the fine particles include a water soluble polymer.

The water soluble polymer can be any water soluble polymer known to those of ordinary skill in the art. For example, in some embodiments, the water soluble polymer is polyethylene glycol.

In a particular embodiment, the material includes 1 to 50 mol % of an amphipathic compound of formula (2):

MOOCR$^3$—CO—HNCH(COOR$^4$)CH$_2$CH$_2$COOR$^4$ where M is a hydrogen atom or a monovalent cation, R$^3$ is —CH$_2$CH$_2$— and R$^4$ is a C$_{10}$-C$_{22}$ alkyl group; and 0.5 to 4.8 mol % of an amphipathic compound including polyethylene glycol as its hydrophilic portion, wherein at least one fine particle has an average particle diameter of 100 to 500 nm.

In certain embodiments, at least one fine particle further includes a drug bound to at least one fine particle. The term "drug" and "therapeutic agent" are used synonymously throughout this application, and refer to any agent that can be applied in the diagnosis, treatment, or prevention of a disease or health-related condition in a subject. For example, in some embodiments, the drug is an agent that can be applied in the diagnosis, treatment, or prevention of a disease of bone, cartilage, or bone marrow in a subject. In other embodiments, the drug is an agent that can be applied in the diagnosis, treatment, or prevention of joint disease in a subject. In particular embodiments, the drug is an agent that can be applied in the diagnosis, treatment, or prevention of bone marrow disease in a subject.

Thus, for example, the present invention is also generally directed to use of any of the materials set forth herein in the diagnosis, treatment, or prevention of a disease of bone, cartilage, or bone marrow in a subject. The present invention is also generally directed to use of any of the materials set forth herein in the diagnosis, treatment, or prevention of a disease of a joint in a subject. The subject can be any subject, such as a mammal or an avian species. In preferred embodiments, the subject is a human subject.

The dosage of the material can be any dose that is known or suspected to be of benefit in preventing, treating, or diagnosing a disease. For example, the dose may be about 0.1 mg to 500 mg of the material per kg of body weight of the subject or greater (wherein the material includes the particle(s) plus the drug bound to the particle(s)), or any narrower range of mg of material per kg of body weight. Determination of a dose of a drug, as discussed in greater detail in the specification below, is dependent upon a number of factors, such as the route of administration, the disease to be treated, and factors specific to the subject. Repeat administration may or may not be required.

The present invention is also generally directed to methods of preventing, treating, or diagnosing a disease of bone, cartilage, or bone marrow in a subject, involving administering to the subject a pharmaceutically effective amount of the any of the materials set forth above. The invention is also generally directed to methods of preventing, treating, or diagnosing a joint disease in a subject, involving administering to the subject a pharmaceutically effective amount of any of the materials set forth herein. The pharmaceutically effective amount of the material can be any dosage of the material as discussed above.

As discussed above, the subject can be any subject, such as a mammal or an avian species. In certain particular embodiments, the subject is a human. For example, the human may be a patient that has a disease of the bone marrow, bone, cartilage, or joints.

The present invention is also generally directed to a kit that includes a predetermined amount of any of the materials set forth herein, and a sealed container.

In the present specification, the weight of the delivery-forming material means the total weight of the materials forming the delivery material without carrying any drug.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or." Throughout this application, the term "about" is used to indicate that a value includes the standard deviation of error for the device and/or method being employed to determine the value.

As used herein in the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

BRIEF DESCRIPTION OF DRAWINGS

The following drawings form part of the present specification and are included to further demonstrate certain aspects of the present invention. The invention may be better understood by reference to one or more of these drawings in combination with the detailed description of specific embodiments presented herein.

FIG. 3 shows the surface modifying degree of carboxylic acid residue-containing vesicles by PEG and the distribution of the vesicles in bone, liver and spleen.

FIG. 4A—1.5 hrs after administration; FIG. 4B—6 hrs after administration.

FIG. 5 shows the profiles of distribution of the carboxylic acid residue-containing vesicles (0.6 mol % of PEG lipids) in bone, liver and spleen with time.

FIG. 6A—Fluorescence localization in double fluorescence-labeled large multilamellar carboxylic acid residue-containing vesicles (0.6 mol % of PEG-lipid) with diameter of ca 10 μm. This observation was performed before extrusion to submicron size to enable observation of the structure within resolution of a confocal microscope. This image indicates that red fluorescence comes from Texas Red-SOD which is encapsulated in inner aqueous phase and green fluorescence comes from $C_1$-BODIPY $C_{12}$ which is embedded in bilayer membrane. FIG. 6B—Confocal scanning images of femoral bone marrow (BM), spleen (S), and liver (L) taken from rabbit at 6 h after i.v. injection of double fluorescence-labeled carboxylic acid residue-containing vesicles (0.6 mol % of PEG-lipid) with size of 247±22 nm in diameter (lipids: 15 mg/kg b.wt.). The scale bars represent 20 μm.

FIGS. 7A and 7B illustrate transmission electron micrographs of femoral bone marrow tissue section, taken from rabbit at 6 h after i.v. injection of carboxylic acid residue-containing vesicles (0.6 mol % of PEG-lipid) (lipids: 15 mg/kg b.wt.). FIG. 7A—Low magnified micrograph representing the bone marrow tissue including macrophage and various bone marrow cells. FIG. 7B—High magnified micrograph of framed region in FIG. 7A. A massive number of vesicles with original diameter (average 270 nm) are trapped in several endosomes or lysosomes of macrophage. Some are indicated by arrows, which shows same position in FIG. 7A and FIG. 7B.

BEST MODE FOR CARRYING OUT THE INVENTION

Figure 1:
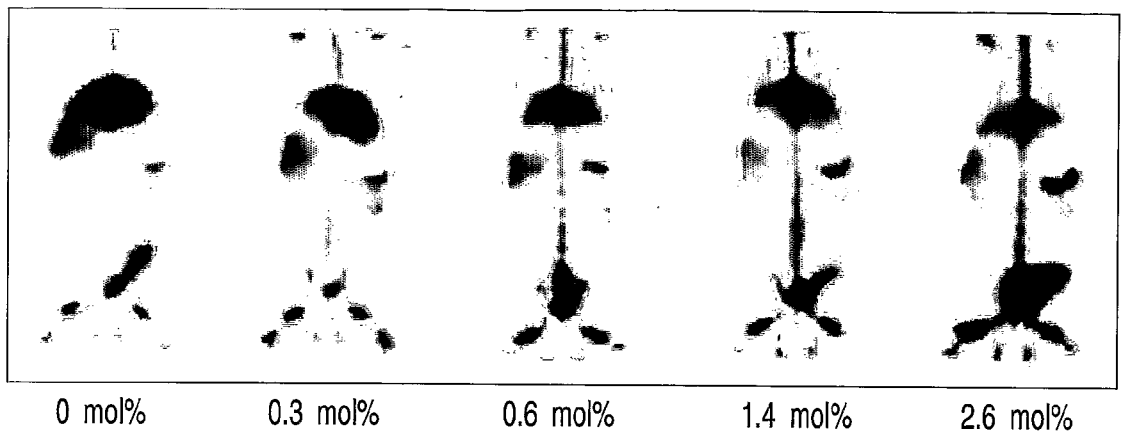
FIG. 1 shows scintigrams of rabbits following intravenous administration of carboxylic acid-containing vesicles. The vesicles contain technetium-99m and are surface modified with PEG lipids at various concentrations.

The present invention generally pertains to bone marrow-directing drug delivery materials that include at least one fine particle comprising an anionic moiety on a surface of the particle.

A. Fine Particles and Amphipathic Compounds

1. Fine Particles

A delivery material for delivering drugs in a living body according to the present invention comprises at least one directional carrier (fine particle) carrying at least one anionic group on its surface. The fine particle can be composed of any substance, so long as the substance carries at least one anionic group on its surface. Examples of such substances include oil droplets, fat emulsions, polymer beads, polymer micelles, polymer gels, protein polymers, and micelles, vesicles, fibrous aggregates and tabular aggregates which are formed by amphipathic molecules. The size of the fine particle is not particularly limited, but is usually 20 to 5000 nm in diameter, preferably 100 to 1000 nm in diameter, and more preferably 250±100 nm in diameter. Administration of a particle over 5000 nm in diameter may cause clogging of capillaries in the lung. In addition, a particle larger than 5000 nm may be trapped within the reticuloendothelial system at the liver or spleen, resulting in the lowering of the expected effects.

The anionic group to be carried on the surface of the delivery material is preferably selected from an anionic group other than a phosphatidylglycerol group, a phospatidylserine group, or a phosphatidyl inositol group. Drug delivery materials containing a phosphatidylglycerol group, a phospatidylserine group or a phosphatidyl inositol group tend to not exhibit directivity to the bone, and thus do not accumulate in the bone. Particular examples of anionic groups used in the context of the present invention include a carboxylic acid group, sulfonic acid group and sulfuric acid group.

Any method of carrying the anionic group on the particle surface is contemplated by the present invention. For example, to carry the anionic group on the particle surface, use may be made of a covalent bond such as an ester bond or an amide bond, physical adsorption of a polymer having the anionic group onto the carrier surface, and incorporation of amphipathic compounds having an anionic group in the hydrophilic moiety as components of an aggregate of amphipathic compounds where the carrier is provided by the aggregate of amphipathic compounds.

Examples of compounds having a sulfonic acid group include taurine, an amino acid having a sulfonic acid group. Taurine can be chemically bonded to the carrier. Alternatively, taurine may be bonded to a hydrophobic moiety to form an amphipathic compound which is then incorporated in the aggregate of molecules. Fatty acids (for example, those described below) can be suitably used as the hydrophobic moiety.

Examples of the compounds having a sulfuric acid group include hyaluronic acid, chondroitin sulfate, dermatan sulfate, keratin sulfate, heparin, and amphiphatic derivatives of these polymers formed by bonding a hydrophobic group to these polymers.

2. Amphipathic Molecules

An amphipathic molecule is defined herein to refer to a molecule having at least one hydrophobic group and at least one hydrophilic group. The amphipathic molecule may, for example, include a carboxylic acid residue, such as a polymeric compound, a surfactant or a phospholipid compound. Preferably, a carboxylic acid residue is located on the surface of the delivery materials to effectively exert the expected advantages, and amphipathic compounds having a carboxylic group in the hydrophilic moiety can be used for this purpose.

Examples of amphipathic compounds having a carboxylic acid residue used in the invention include saturated straight chain fatty acids such as caprylic acid, undecanoic acid, lauric acid, dodecanoic acid, tridecanoic acid, myristic acid, pantadecanoic acid, palmitic acid, margaric acid, stearic acid, nonadecanoic acid, arachidic acid, behenic acid, lignoceric acid, cerotic acid, montanic acid, and melissic acid. Other examples include unsaturated straight chain fatty acids such as obtusilic acid, linderic acid, tsuzuic acid, physeteric acid, palmitoleic acid, petroselinic acid, erucic acid, oleic acid, elaidic acid, vaccenic acid, linoleic acid, nervonic acid, linoelaidic acid, linolenic acid, γ-linolenic acid, bishomo-γ-linolenic acid, and arachidonic acid. Branched chain analogs thereof may also be used. Examples of branched chain fatty acids include iso-acids such as isolauric acid, isomyristic acid, isopalmitic acid and isostearic acid and isoarachidic acid, and antiso acids such as 9-methylundecanoic acid, 10-methyldodecanoic acid, 11-methyltridecanoic acid, 12-methyltetradecanoic acid, 13-methylpentadecanoic acid, 14-methylhexadecanoic acid, 15-methylheptadecanoic acid, and 16-methyloctadecanoic acid.

The amphipathic compounds having a hydrophilic group with a carboxylic acid residue at the terminal thereof, bonded to a hydrophobic group through an optional spacer, can be represented by formula (1):

MOOC—(R$^1$)$_p$—R$^2$ where M is a hydrogen atom or a monovalent cation, R$^1$ is a spacer, R$^2$ is a hydrophobic group, and p is 0 or 1. The spacer (R$^1$) may be present (p=1) or may not be present (p=0). However, the spacer is preferably present in case where the carboxylic acid residue is shielded by the hydrophilic group of the amphipathic compound used as the other components of the delivery materials, in which case the bone directivity is lowered. Examples of the spacer include —(CH$_2$)$_n$— (n is an integer of 1 to 5), —(CH$_2$CH$_2$O)$_n$— (n is an integer of 1 to 115), and —CH$_2$OCH$_2$—. Examples of the hydrophobic group (R$^2$) include a hydrophobic peptide, an alkyl group, a sterol group such as cholesterol, a diacyl derivative of an amino acid. The hydrophobic group is selected taking into consideration the balance between the hydrophilicity and hydrophobicity, and compatibility with the amphipathic compounds used as the other components of the delivery materials. Examples of the monovalent cation (M) include alkali metals such as sodium and potassium.

In certain embodiments, the amphipathic compound is a lipid compound. Examples of a lipid compound having a carboxylic acid group includes those lipid compounds which can be prepared by reacting an amino dicarboxylic acid, such as glutamic acid or aspartic acid, with a C$_{12}$-C$_{22}$ long chain alcohol, and reacting the remaining amino group with dicarboxylic acid such as succinic acid, methylsuccinic acid or fumaric acid. Preferred carboxylic acid-containing lipid compounds can be represented by formula (2):

MOOCR$^3$—CO—HNCH(COOR$^4$)CH$_2$CH$_2$COOR$^4$ where M is a hydrogen atom or a monovalent cation, R$^3$ represents —CH$_2$CH$_2$— or —CH(CH$_3$)CH$_2$—, and R4 represents a C$_{12}$-C$_{22}$ alkyl group. Examples of the monovalent cation (M) include alkali metals such as sodium and potassium. These carboxylic acid-containing lipid compounds can be synthesized by the method described in U.S. Pat. No. 5,370,877, herein specifically incorporated by reference. Additional examples of amphipathic compounds having a carboxylic acid group are described in WO 2003/018539, herein specifically incorporated by reference. However, amphipathic compounds having a carboxylic acid group should not be limited to those mentioned above.

3. Vesicles

In certain embodiments of the present invention, the fine particle includes an aggregate of amphipathic molecules forming a vesicle. The vesicles of the present invention preferably contain a neutral lipid compound in addition to the above negatively charged group-containing lipid compound. Any lipid molecules which are entirely not charged positive or negative may be used as the neutral lipid compound. Phospholipids containing phosphatidylcholine group are preferred. Phospholipids containing phosphatidylcholine group include saturated phospholipids and unsaturated phospholipids, and any of these can be used in the present invention. Any combination of these compounds may also be used. Examples of the saturated phospholipid include synthesized and semi-synthesized phospholipids, and natural lipids or derivatives thereof, including hydrogenated egg yoke lecithin and hydrogenated soybean lecithin having a hydrogenation degree of nearly 100%, as well as dimyristoylphosphatidylcholine, dipalmitoylphosphatidylcholine and distearoylphosphatidylcholine. Examples of the unsaturated phospholipids include egg yolk lecithin, soybean lecithin, and polymerizable phospholipids having a polymerizable group such as 1,2-bis(2,4-octadecadienoyl)-sn-glycero-3-phosphocholine or 1,2-bis(8, 10,12-octadecatrienoyl)-sn-glycero-3-phosphocholine. The polymerizable phospholipid may contain a non-polymerizable fatty acid residue such as linear or branched alkyl, acyl, non-polymerizable alkenyl or non-polymerizable alkenoyl group having 2 to 24 carbon atoms.

The amount of the negatively charged group-containing lipid compound in the membrane forming material that constitutes the vesicle of the present invention is preferably 1 to 50 mol %, more preferably 5 to 20 mol %. If the amount of the negatively charged group-containing lipid compound is less than 1 mol %, the effect of the negatively charged group is lowered. On the other hand, if the amount of the negatively charged group-containing lipid compound is more than 50 mol %, the resultant vesicles may become unstable, which is not preferable.

The membrane forming material that constitutes the vesicles of the present invention may contain a cholesterol compound as a stabilizer of the vesicle membranes. Examples of the cholesterol compound include ergosterol and cholesterol. Cholesterol is preferred. The amount of the cholesterol compound is not particularly limited, but is preferably 40 to 100 mol in ratio to each 100 mol of the membrane forming amphiphiles as required for the formation of a stable vesicle. The neutral lipid compound described above may occupy 99 mol % or less of the amount of the amphipathic compounds forming the vesicles of the present invention.

Further, by incorporating a PEG modified lipid compound in the membrane forming material, bone marrow selectivity of the resultant vesicles is enhanced. The weight-average molecular weight of the PEG chain which is bonded to a lipid compound to modify the lipid compound is preferably 1000 to 20000. The terminal of the PEG chain may be constituted by acetyl, methoxy, carboxyl and/or hydroxyl group. The lipid compound to which PEG is bonded is not particularly limited. Such a PEG modified phospholipid is described in, for example, Woodle and Lasic, Biochem. Biophys. Acta, 1113(2):171-199, 1992 and WO 2001/016211 and WO 2001/016211, each of which is herein specifically incorporated by reference. The content of the PEG modified amphipathic compound varies depending on its molecular weight. However, the PEG modified amphipathic compound is preferably used in an amount of 0.1 to 10 mol % based on the total amount of the amphipathic compounds constituting the vesicles. If the content of the PEG modified amphipathic compound is small, efficiency of accumulation of the delivery materials on the bone is lowered due to the uptake into the liver or spleen. On the other hand, if the content of the PEG modified amphipathic compound is large, the anionic group is shielded and the bone directivity is lowered. Thus, to reduce the incorporation into the liver in particular, and thus to improve the accumulation in the bone, it is preferable that the PEG modified amphipathic compound makes up 0.6 to 4.8 mol % of the total amount of the amphipathic compounds forming the vesicles.

The vesicles of the present invention may be prepared by any method known in the art. For example, the powder of the lipid mixture can be added with an aqueous solvent to hydrate and swell, which is then made into the desired vesicles by stationary hydration method, by using a vortex mixer, forced stirrer, ultrasonic applicator, homogenizer, microfluidizer or high pressure extruder, by freeze-thaw method, or by organic solvent injection method, surfactant removal method, reverse phase evaporation method or organic solvent droplet evaporation method. Generally, vesicles are classified into multi-layered vesicles and unilamellar vesicles dependent on the preparation conditions, but any of them can be used in the present invention. The vesicles of the present invention has an average diameter of usually 50 to 5000 nm, preferably 100 to 1000 nm, more preferably 250±100 nm, though the diameter is not limited thereto. Administration of vesicles having an average diameter larger than 5000 nm may induce clogging of blood capillaries of the lung. On the other hand, when the average diameter of the vesicles is larger than 1000 nm, the effect of the invention as noted above may be lowered due to trapping within the reticuloendothelial system of the liver and spleen to a very large extent.

B. Drugs

In particular aspects of the present invention, at least one fine particle of the material includes a drug bound to the fine particle. The term "drug" and "therapeutic agent" are used synonymously throughout this application, and refer to any agent that can be applied in the diagnosis, treatment, or prevention of a disease or health-related condition in a subject. The drugs to be carried by the delivery materials of the present invention are selected from those suitable for the prevention, diagnosis, therapy or protection of bone, bone marrow or joint diseases, and is not particularly limited. Preferably, the delivery materials carry drugs selected from an antiviral agent, an antimicrobial agent, antibacterial agent, an antifungal agent, an antineoplastic agent, an anti-inflammatory agent, a radio-labeling agent, a radio-opaque compound, a phosphor compound, a dyestuff compound, a nucleic acid sequence, an anticancer agent, a growth factor, a hematinic factor (e.g., erythropoietin, G-CSF) and a physiologically active substance. To carry these drugs, any suitable method can be used taking the properties of the carrier and the drugs into consideration. For example, the drugs can be carried by the carrier utilizing a covalent bonding, or a secondary interaction such as hydrogen bonding, hydrophobic interaction and ionic bonding. When the carrier is constituted by the vesicle, the carrying method can be selected from incorporation in the inner aqueous phase of the vesicle, introduction into the hydrophobic portion of the vesicle membrane, and bonding to, or adsorption on the vesicle surface, taking the properties of the drugs to be carried.

Any drug or therapeutic agent is contemplated for delivery by the delivery material of the claimed invention. Specific examples of antiviral drugs include oseltamivir phosphate and indinavir sulfate. Antimicrobials include antibacterials such as ciprofloxacin, defotetan and azithromycin, antifungals such as amphotericin B, nystatin and ketoconazole and anitubercular agents such as isoniazid, streptomycin and rifampin. Agents to stimulate bone growth or protect against bone loss such as vitamin D, calcium, PTH antagonists or bisphosphonates are also contemplated.

Anti-neoplastic agents are also contemplated as drugs for delivery by the materials of the present invention. A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. In particular embodiments, the chemotherapeutic agent is selected from the group consisting of doxorubicin, topoisomerase I inhibitors such as topotecan and irinotecan and mitotic inhibitors such as paclitaxel and etoposide, and antimetabolites such as methotrexate and monoclonal antibodies such as rituximab.

Stimulators of red cell production are also contemplated for delivery, and include iron, epoetin alfa, and filgrastim. Agents to protect bone marrow from radiation and chemotherapy induced damage are also contemplated, and include amifostin, natural antioxidants such as vitamin e and phenol containing natural products such as curcumin as well as methotrexate rescue agents such as leucovorin.

The drug may be an agent used to remove heavy metals from bone marrow, such as pentetate calcium trisodium. Anti-inflammatory agents such as prednisone, hydrocortisone, aspirin, indomethacin, celecoxib, and ibuprofen are also contemplated for delivery, as are radiolabeled agents such as $^{99m}$Tc, $^{111}$In, $^{186}$Re and $^{188}$Re. Radio-opaque compounds such as iodine-containing CT contrast agents are also contemplated for delivery, as are MRI diagnostic agents such as gadopentetate dimeglumine.

C. Dosage and Administration

The phrases "pharmacologically effective" or "pharmaceutically acceptable" refer to molecular entities and compositions that do not produce an adverse, allergic or other untoward reaction when administered to an animal, or a human, as appropriate. As used herein, "pharmaceutical preparation" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

An effective amount of the therapeutic or preventive agent is determined based on the intended goal, for example, treatment of a bone disease. The quantity to be administered, both according to number of treatments and dose, depends on the subject to be treated, the state of the subject and the protection desired. Precise amounts of the material of the present invention also depends on the judgment of the practitioner and may be specific to each individual.

In certain embodiments, it may be desirable to provide a continuous supply of the material to the patient. For topical administrations, repeated application would be employed. For various approaches, delayed release formulations could be used that provide limited but constant amounts of the therapeutic agent over an extended period of time. Continuous perfusion of the region of interest may be preferred in certain instances. The administration could be post-operative, such as following surgical excision of a bone tumor.

The dosage and method of administration of the materials of the present invention vary depending on the subject to be treated and the object to be achieved, and is thus not particularly limited. For example, the vesicles can be administered intravenously, subcutaneously, intramuscularly, intraarticularly, or topically. The dose amount of the material (including drug) that is administered may be any pharmaceutically effective amount that is known or suspected to be of benefit in the treatment, prevention, or diagnosis of a disease in a subject. For example, the dose amount may be 0.1 mg/kg to 500 mg/kg body weight, or higher. In particular embodiments, the dose amount is 0.1 to 500 mg/kg body weight of the subject, based on the total amount of the drug delivery material, including presence of the drug in the drug delivery material. When the dose amount is less than 0.1 mg/kg, the effect of the invention may not be obtained. On the other hand, when the vesicles are administered in a larger amount, it takes longer for the vesicles to be taken up in the bone tissues, increasing the amount of the vesicles accumulating in the liver or spleen.

D. Diseases to be Prevented, Treated, or Diagnosed

The delivery materials of the present invention can be utilized in the diagnosis, treatment, or prevention of any disease or health-related condition. For example, in particular aspects of the present invention, the disease is a disease that affects the bone marrow, bone, cartilage, or a joint.

For example, the delivery material of the present invention can be used as an ossification promoting agent, a bone disease preventing or treating agent, a fracture preventing or treating agent, a chondrogenesis promoting agent, a cartilage disease preventing or treating agent, or a preventing or treating drug for cartilage diseases such as osteoarthritis, or chronic joint rheumatism, injuries such as fracture, dislocation and bone breakage, inflammatory diseases such as periostitis, tuberculous arthritis, syphilitic bone inflammation, bone deformation due to Hansen disease, actinomycosis, blastomycosis and brucellosis, tumors such as benign osteoma, osteochondroma, osteoid osteoma, multiple osteocartilaginous exostosis, solitary bone cyst, giant cell tumor of bone, fibrous bone dysplasia, histiocytosis X of bone, parosteal osteosarcoma, osteosarcoma, chondrosarcoma, fibrosarcoma of bone, Ewing sarcoma, multiple myeloma and bone metastasis of cancer, metabolic and endocrine diseases such as rickets, osteomalacia, scurvy, hyperthyroidism, Paget disease, abnormal pituitary function, iron deficiency anemia, fibrochondritis, renal osteodystrophy, osteoporosis, bone defect and rigidity myelitis, or acquired skeletal dysplasia or malformation syndromes such as achondroplasia, acraniocleidoplasia, deforming osteodysplasty, dysosteogenesis, osteopetrosis, craniosynostosis, dens hypoplasia, Klippel-Feil syndrome, rachischisis, hemivertebra, bone abnormality-spondylosis deformans, scoliosis, and Perthes disease.

The delivery material of the present invention can also be suitably used for highly efficient delivery of preventive or diagnostic drugs for bone marrow diseases such as osteomyelitis, myeloid leukemia, multiple myeloma, dyshematopoiesis, ion deficiency anemia, pernicious anemia, megaloblastosis, hemolytic anemia, herediary spherocytosis, drepanocytic anemia and aplastic anemia, or delivering erythropoietin produced by genetic recombination as a drug for remedying renal disease-associated anemia, therapeutic drug for granulocytopenia used in carcinostatic therapies, and colony-stimulating factor (CSF) applied to bone marrow transportation and acquired immunodeficiency syndrome (AIDS). Examples of therapeutic agents for myelogenetic tumors include cytarabine, daunorubicin, idarubicin, aclarubicin, mitoxantrone, enocitabine, 6-mercaptopurine, thioguanine, azacytidine, amsacrine, steroid, arsenious acid, hydroxycarbamide, hydrea, cytosine arabinoside, anthracycline medicines, retinoic acid, vinca alkaloid medicines, predonine, L-asparaginase, interferon, melphalan, vincristine, adriamycin, endoxan, methotrexate, thalidomide, etoposide, cyclophosphamide, carmustine, dexamethasone, cytokine, interferon formulations, busulfan, hydroxyurea, mesyl acid imatinib, prednisolone and bortezomib.

The delivery material of the present invention, when it carries a gamma emitting or positron emitting radioisotope, may be used as a diagnostic agent for bone or bone marrow diseases. The delivery material of the present invention could also carry therapeutic radionuclides (Auger electron, beta emitting or alpha particle emitting) for radionuclide therapy of bone or bone marrow diseases. Further, the delivery material of the present invention, when it carries a radio-opaque agent, may be used as a diagnostic agent for X-ray and X-ray computed tomography. The delivery material of the present invention, when it carries a superparamagnetic or paramagnetic agent, may be used as a diagnostic agent for magnetic resonance imaging. In addition, since the delivery material of the present invention can carry a gene and introduce it into the bone marrow with high efficiency, the delivery material can transport, e.g., a drug tolerant gene to the bone marrow to protect the bone marrow in an auxiliary therapy for therapy using an anticancer agent.

E. Secondary Treatment

In some aspects of the present invention, the materials of the present invention are applied in the prevention, diagnosis, or treatment of a disease, such as a disease of bone, bone marrow, cartilage, or a joint. A wide variety of therapies, known to one of skill in the art, may be used in combination with the materials of the present invention. Examples of such therapies include radiation therapy, chemotherapy, surgical therapy, immunotherapy, gene therapy, phototherapy, cryotherapy, toxin therapy, or hormonal therapy. One of skill in the art would know that this list is not exhaustive of the types of treatment modalities available for cancer and other hyperplastic lesions.

In order to increase the effectiveness of a drug, it may be desirable to combine the materials of the present invention with other agents effective in the treatment of disease. These compositions would be provided in a combined amount effective to achieve a desired result, such as treatment of a disease that affects bone marrow. This process may involve administering a single composition or pharmacological formulation to a subject that includes both agents, or administering two distinct compositions or formulations, at the same time, wherein one composition includes the material of the present invention and the other includes the second agent.

Alternatively, the administration of the material may precede or follow the other agent treatment by intervals ranging from minutes to weeks. In embodiments where the other agent and the material of the present invention are administered separately, one would generally ensure that a significant period of time did not expire between the time of each delivery. In such instances, it is contemplated that one may administer both agents within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Administration of the materials of the present invention to a subject will follow general protocols for the administration of pharmaceutical agent. It is expected that the treatment cycles would be repeated as necessary. It also is contemplated that various standard therapies, as well as surgical intervention, may be applied in combination with the described materials set forth herein.

F. Kits

The drug delivery material of the present invention may be assembled in a kit. The kit will include one or more container. The container of the kits will generally include at least one vial, bag, test tube, flask, bottle, or other container, into which a component may be placed, and preferably, suitably aliquoted. One or more of the containers may comprise a pharmaceutically effective amount of the drug delivery material of the present invention. In some embodiments of the present invention, the drug delivery material may include one or more drugs. In other embodiments, the drug is comprised in a first container, and the drug delivery container is comprised in a second container, which can be combined prior to administration.

Where there is more than one component in the kit, the kit also will generally contain additional containers into which the additional components may be separately placed. However, various combinations of components may be comprised in a container. The kits of the present invention also will typically include a means for packaging the component containers in close confinement for commercial sale. Such packaging may include injection or blow-molded plastic containers into which the desired component containers are retained.

EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute some modes for its practice. However, those of skill in the art should, in light of the present disclosure, appreciate that many changes can be made in the specific embodiments which are disclosed and still obtain a like or similar result without departing from the spirit and scope of the invention.

Example 1

Carboxylic Acid Group-Containing Vesicles

Dipalmitoylphosphocholine and cholesterol were purchased from Nippon Fine Chemical Co. Ltd. (Osaka, Japan); 1,2-distearoyl-sn-glycero-3-phosphoethanolamine-N-[monomethoxy poly(ethylene glycol) (5000)] (PEG-DSPE) was purchased from NOF Co. (Tokyo, Japan). The compound of formula (2) in which $R^3$ represents —$CH_2CH_2$—, and $R^4$ represents hexadecyl was synthesized as previously reported (Sou et al., Biotechnol. Prog., 19:1547-1552, 2003). Glutathione was purchased from Sigma (St. Louis, Mo.). All vesicle preparations were performed under sterile conditions. Dipalmitoylphosphocholine (45.5 mol %), cholesterol (45.5 mol %) and a carboxylic acid group-containing lipid compound (compound of formula (2) in which $R^3$ represents —$CH_2CH_2$—, and $R^4$ represents hexadecyl; 9.0 mol %) were dissolved in t-butanol, and the mixture was freeze-dried to prepare mixed lipid powder. The powder was dispersed into an aqueous sodium hydroxide (NaOH) solution and stirred at 25° C. to prepare an aqueous dispersion of multi-layered vesicles. This dispersion was frozen by liquid nitrogen and then thawed at 40° C. This freeze-thaw cycle was repeated three times to prepare a dispersion of vesicles. The dispersion was freeze-dried to prepare a vesicle composition. Glutathione solution (30 mM) was added and the composition was stirred at 25° C. for 2 hours. The resultant mixture was placed into an EXTRUDER™ (available from Nichiyu Liposome, Japan) and sequentially passed through acetyl cellulose filters (available from Fuji Photo Film, Japan) having pore sizes of 3.0 µm, 0.8 µm, 0.65 µm, 0.45 µm, 0.30 µm, and 0.22 µm, respectively, under pressure (2 MPa) at 14° C., thereby preparing a vesicle dispersion. The unencapsulated glutathione was removed by three ultracentrifugation steps ($3\times10^5$ g, 60 min each) and the vesicles were dispersed in saline solution.

Surface modification with PEG was performed by making use of the spontaneous incorporation of PEG-DPSE into vesicles (Sou et al., Bioconjug. Chem., 11:372-379, 2000). This vesicle dispersion was added with an aqueous dispersion of PEG-lipid (PEG bonded distearoylphosphoethanolamine (PEG-DSPE)). The mixture was allowed to stand at 37° C. for 2 hours and centrifuged (300000 g, 1 hour) to remove free PEG-DSPE. The precipitated vesicles were dispersed into physiological saline to prepare a desired vesicle dispersion. The amount of PEG-DSPE incorporated was determined from the peak area ratio of methylene protons of PEG-DSPE (3.63 ppm) to the choline methyl protons of DPPC (3.39 ppm) using $^1$H-NMR spectroscopy (JEOL JNM-LA500), and the diameter of the resulting vesicles was determined with a COULTER submicron particle analyzer (N4SD, Coulter, Hialeah, Fla.), and represented as an average diameter±standard deviation (SD) as shown in Table 1.

TABLE 1

PEG-DSPE Content and Diameter

| Sample No. | PEG5000-DSPE Content (mol %) | diameter (nm) |
|---|---|---|
| 1 | 0 | 269 ± 11 |
| 2 | 0.3 | 276 ± 13 |
| 3 | 0.6 | 273 ± 12 |
| 4 | 1.4 | 275 ± 12 |
| 5 | 2.6 | 274 ± 12 |

Example 2

Carboxylic Acid Group-Containing Vesicles Incorporating a Radioactive Label Substance A solution of radioisotope [technetium-99 m] sodium pertechnetate ($^{99m}TcO_4$; half-life: 6 hours) in physiological saline was added to a commercially available kit of freeze-dried hexamethylpropyleneamine oxime (HMPAO), and the solution was mixed with the carboxylic acid group-containing vesicle dispersion of Example 1 (Rudolph et al., Proc. Natl. Acad. Sci. USA, 88:10976-10980, 1991; Phillips et al., Nucl. Med. Biol., 19:539-547, 1992; Phillips et al., J. Pharmacol. Exp. Ther., 288:665-670, 1999; Sou et al., J. Pharmacol. Exp. Ther., 312:702-709, 2005; U.S. Pat. Nos. 5,143,713 and 5,158,760). The resultant mixture was allowed to stand for 1 hour, and the free $^{99m}$Tc-HMPAO was removed by gel filtration, thereby preparing a vesicle dispersion incorporating the radioactive label substance therein. As indicated in Table 2, 80% or more of the radioactive label substance was incorporated in the vesicles.

TABLE 2

Labeling Efficiency of Carboxylic Acid Group-Containing Vesicle

| Sample No. | Labeling efficiency (%) |
|---|---|
| 1 | 83.6 |
| 2 | 83.6 |
| 3 | 84.6 |
| 4 | 84.1 |
| 5 | 83.2 |

Example 3

Scintigraphy after Administration of Carboxylic Acid Group-Containing Vesicles

Male New Zealand White rabbits (2-3 kg, n=3-4 per each vesicle formulation) were anesthetized with an intramuscular injection of ketamine/xylazine (both from Phoenix Scientific, St. Joseph, Mo.) mixture (50 and 10 mg/kg body weight (b.w.), respectively). One ear of a rabbit was catheterized with a venous line, and the other ear was catheterized with an arterial line. $^{99m}$Tc-vesicle dispersion prepared in Example 2 was infused into the venous line at 1 mL/min and blood samples were drawn from the arterial line. Each rabbit received a total dose of 214.6-377.4 MBq (5.8-10.2 mCi) $^{99m}$Tc-activity and 15 mg/kg body weight of lipids. Rabbits were placed in the supine position under a Picker (Cleveland, Ohio) large-field-of-view gamma camera using a low-energy all-purpose collimator and interfaced with a Pinnacle imaging computer (Medasys, Ann Arbor, Mich.).

Figure 2:
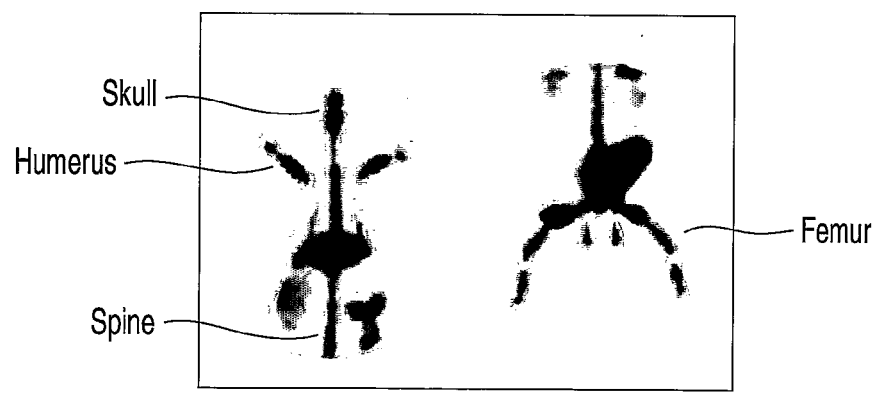
FIG. 2 shows whole body scintigrams of rabbits 24 hours after administration of carboxylic acid-containing vesicles which contain technetium-99m (2.6 mol % of PEG lipids).

The gamma camera images (scintigrams) 24 hours after the administration are shown in FIG. 1. At the upper portion of each scintigram, the amount of PEG-lipid are indicated (0, 0.3, 0.6, 1.4 and 2.6 mol %). From FIG. 1, it is seen that the skeleton including the spine and femora can be clearly visualized, and that remarkable bone selectivity can be confirmed at a dose of 0.6 mol % or more of PEG-lipid. FIG. 2 shows scintigrams (whole body images) 24 hours after the carboxylic acid group-containing vesicle (PEG-lipid content: 2.6 mol %) was administered to a rabbit. As can be seen from FIG. 2, the directivity noted above was confirmed to include bones throughout the entire body.

Example 4

Accumulation Rate in the Bone after Administration of Radioactively Labeled Carboxylic Acid Group-Containing Vesicles The radioactively-labeled vesicle dispersion prepared in Example 2 was administered to a rabbit (lipid dose amount: 15 mg/kg body weight) through the ear vein. The animals were rapidly sacrificed at 24 h and the tissue samples were collected, weighed and counted for radioactivity in the same scintillation well counter for calculation of biodistribution. Bone mass was estimated to be 12 times that of one femur (Deitz, Proc. Soc. Exp. Med., 57:60-62, 1944). The amount of the radioactive substance accumulated in the liver, spleen and bones was measured. Results are shown in FIG. 3. As can be seen from FIG. 3, high accumulation in the bones are confirmed, and the percent injected dose (ID) in the bones is increased and the percent ID in the spleen is lowered when 0.6 mol % or more of PEG-lipid is introduced. The percent of ID is calculated from the radioactivity measured in the excised organs as percentage when the total administered amount is set at 100%.

Example 5

Vesicles not Containing a Negatively Charged Component

A vesicle composition consisting of dipalmitoyl phosphatidylcholine (50 mol %) and cholesterol (50 mol %) was radioactively labeled as in Example 2. The resulting vesicle dispersion was administered to a rabbit (lipid dose amount: 15 mg/kg body weight). At 24 hours after the administration, the amount of the radioactive substance accumulated in the liver, spleen and bones were measured, and the bone selectivity ratio was calculated. Results are shown in Table 3A below. As indicated in Table 3A, the bone selectivity ratio of 0.05 for this vesicle formulation is very low, since large part of the vesicles accumulated in the liver and spleen.

Example 6

Vesicles Containing Negatively Charged Lipid

A vesicle composition consisting of dipalmitoyl phosphatidylcholine (45.5 mol %), cholesterol (45.5 mol %) and dipalmitoyl phosphatidylglycerol (9.0 mol %) was radioactively labeled as in Example 2. The resulting vesicle dispersion was administered to a rabbit (lipid dose amount: 15 mg/kg body weight). At 24 hours after the administration, the amount of the radioactive substance accumulated in the liver, spleen and bones were measured, and the bone selectivity ratio was calculated. Results are shown also in Tables 3A below. As indicated in Tables 3A, the bone selectivity ratio of 0.16 for this vesicle formulation is very low, since a large part of the vesicles accumulated in the liver and spleen.

TABLE 3A

Composition of Vesicles and Bone selectivity

| Ex. No. | Composition of vesicles | Bone selectivity ratio |
|---|---|---|
| Ex. 5 | Dipalmitoylphosphatidylcholine (50 mol %), and cholesterol (50 mol %) | 0.05 |
| Ex. 6 | Dipalmitoylphosphatidylcholine (45.5 mol %), cholesterol (45.5 mol %) and dipalmitoylphosphatidylglycerol (9.0 mol %) | 0.16 |

Bone selectivity ratio = bone (%)/{liver (%) + spleen (%)}

Table 3B below shows the bone selectivity ratios of Samples 1-5 of Example 2.

TABLE 3B

Composition of Vesicles and Bone selectivity

| | Ex. No. | Composition of vesicles | Bone selectivity ratio |
|---|---|---|---|
| Ex. 2 | Sample 1 | Dipalmitoylphosphatidylcholine (45.5 mol %), cholesterol (45.5 mol %) and carboxylic acid type lipid (9.0 mol %) | 1.00 |
| | Sample 2 | Dipalmitoylphosphatidylcholine (45.5 mol %), cholesterol (45.5 mol %) and carboxylic acid type lipid (9.0 mol %) + PEG-DSPE (0.3 mol %) | 1.15 |
| | Sample 3 | Dipalmitoylphosphatidylcholine (45.5 mol %), cholesterol (45.5 mol %) and carboxylic acid type lipid (9.0 mol %) + PEG-DSPE (0.6 mol %) | 1.95 |
| | Sample 4 | Dipalmitoylphosphatidylcholine (45.5 mol %), cholesterol (45.5 mol %) and carboxylic acid type lipid (9.0 mol %) + PEG-DSPE (1.4 mol %) | 2.91 |
| | Sample 5 | Dipalmitoylphosphatidylcholine (45.5 mol %), cholesterol (45.5 mol %) and carboxylic acid type lipid (9.0 mol %) + PEG-DSPE (2.6 mol %) | 2.04 |

Bone selectivity ratio = bone (%)/{liver (%) + spleen (%)}

Example 7

Figure 4A:
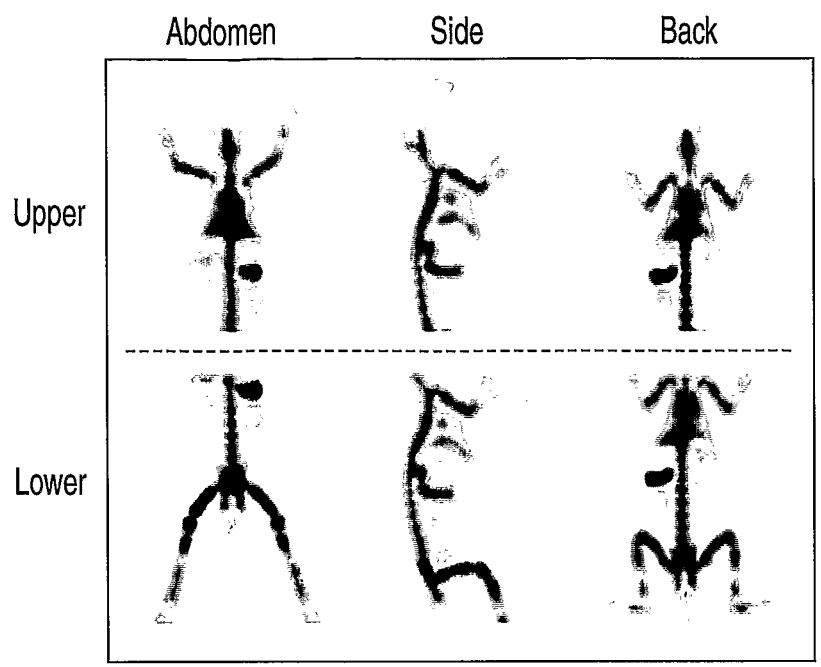
FIGS. 4A and 4B show scintigrams 1.5 and 6 hours after administration of carboxylic acid-containing vesicles which contain technetium-99m (0.6 mol % of PEG lipids).
Figure 4B:
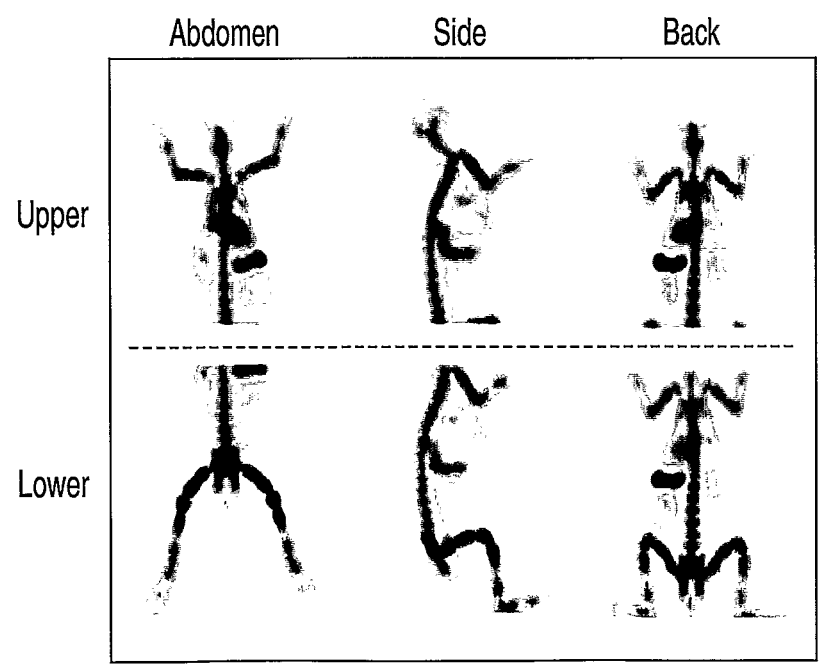

Profiles of Distribution of the Carboxylic Acid Residue-Containing Vesicles in Bone with Time The carboxylic acid residue-containing vesicles which are comprised of dipalmitoylphosphatidylcholine (45.5 mol %), cholesterol (45.5 mol %) and a carboxylic acid group-containing lipid compound (compound of formula (2) in which $R^3$ represents —$CH_2CH_2$—, and $R^4$ represents hexadecyl; 9.0 mol %) and PEG-DSPE (0.6 mol %) were prepared according to the method described in Example 1, and the labeling of the vesicles with radioisotope [technetium-99 m] HMPAO ($^{99m}$Tc-HMPAO; half-life: 6 hours) was performed according to the method described in Example 2. This vesicle dispersion was intravenously administered to a rabbit (lipid dose amount: 15 mg/kg body weight) through the ear vein, and the gamma camera images (scintigrams) of the whole body were taken during 6 hours after the administration. One-minute dynamic 64×64 pixel scintigraphic images were acquired over a continuous period of 1.5 h after the injection of $^{99m}$Tc-vesicles. Static images were also acquired at various times post-injection. The image analysis was performed using a nuclear medicine analysis workstation (Pinnacle computer; Medasys, Ann Arbor, Mich.). The regions of interest were drawn around images of the whole body, one femur, liver, and spleen. The radioactivity counts were decay-corrected at each time, and converted to a percentage of whole body counts. Corrections were made for the blood pool contribution of each organ using the percent injected dose (% ID) measured immediately after infusion. FIGS. 4A and 4B are the scintigrams at 1.5 hours (FIG. 4A) and 6 hours (FIG. 4B) after administration. The profiles of the distribution of administered vesicles in bone, liver, and spleen was analyzed from the scintigrams and shown in FIG. 5. The vesicle distribution ratio in bone was increased after administration and reached 68.55±3.31% (n=3) at 6 hours.

The animals were rapidly sacrificed at 6 h and the tissue samples were collected, weighed and counted for radioactivity in the same scintillation well counter for calculation of biodistribution. To calculate the % ID per organ, total blood volume, muscle and skin mass were estimated as 5.7%, 45%, and 10% of total body weight, respectively (Kozma et al., Anatomy, physiology, and biochemistry of the rabbit, in the Biology of the Laboratory Rabbit, Weisbroth et al. (Eds.), 50-69, Academic Press, NY, 1974; Kaplan and Timmons, The Rabbit: A Model for the Principles of Mammalian Physiology and Surgery, Academic Press, NY, 1979). Bone mass was estimated to be 12 times that of one femur (Deitz, Proc. Soc. Exp. Med., 57:60-62, 1944). The percent of ID is calculated from the radioactivity measured in the excised organs as a percentage when the total administered amount is set at 100%. As shown in Table 4, 69.74±0.86% (n=3) of the administered vesicles was detected in bone.

TABLE 4

Distribution of the Technetium-99m Labeled Vesicles in Organs (6 hours after administration).

| Organs | Percent of injected dose (%) | Percent of injected dose per gram of organ (%/g) |
| --- | --- | --- |
| Blood | 6.58 ± 2.91 | 24.13 ± 0.65 |
| Bone | 69.74 ± 0.86 | 14.13 ± 0.40 |
| Liver | 11.51 ± 2.88 | 13.05 ± 0.38 |
| Spleen | 5.00 ± 1.19 | 9.18 ± 0.37 |
| Bowels | 5.85 ± 0.31 | 4.16 ± 0.35 |
| Skin | 1.57 ± 0.21 | 2.29 ± 0.12 |
| Kidney | 2.40 ± 0.10 | 3.35 ± 0.08 |
| Muscle | 1.86 ± 0.17 | 1.98 ± 0.27 |
| Lung | 0.19 ± 0.03 | 0.54 ± 0.03 |
| Heart | 0.03 ± 0.01 | 0.16 ± 0.01 |
| Brain | 0.01 ± 0.00 | 0.09 ± 0.01 |
| Testis | 0.03 ± 0.01 | 0.09 ± 0.01 |

Example 8

Distribution of Vesicles in Bone

One femur in Example 7 was roughly separated to the diaphysis and epiphysis, and the diaphysis was further separated to the bone marrow and skeleton. The radioactivity in each tissue was counted. As shown in Table 5, 66.5±0.9% of the radioactivity was detected in bone marrow meaning that the carboxylic acid residue-containing vesicles especially have directivity to bone marrow.

TABLE 5

Distribution of the Technetium-99m labeled vesicles in bone marrow, epiphysis, and skeleton of one femur

| Bone parts | Percent of radioactivity (%) |
| --- | --- |
| Bone marrow | 66.5 ± 1.1 |
| Epiphysis | 28.8 ± 1.3 |
| Skeleton | 4.7 ± 0.3 |

Example 9

Figure 6A:
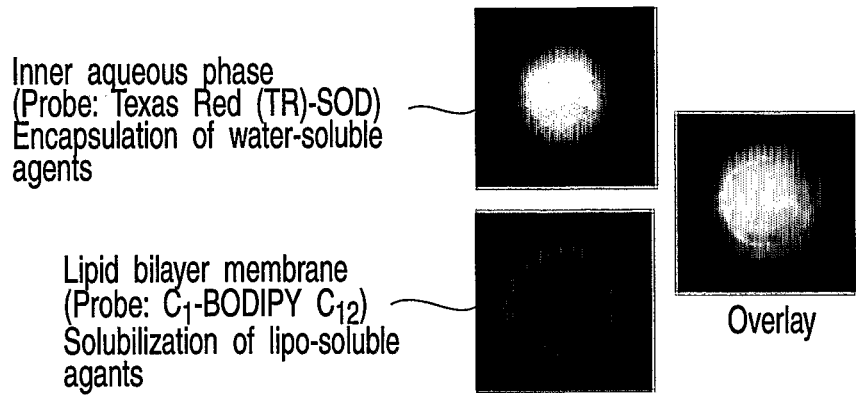
FIGS. 6A and 6B illustrate histological examination of fluorescence delivered into bone marrow tissues using carboxylic acid residue-containing vesicles (0.6 mol % of PEG-lipid) as carriers.
Figure 6B:
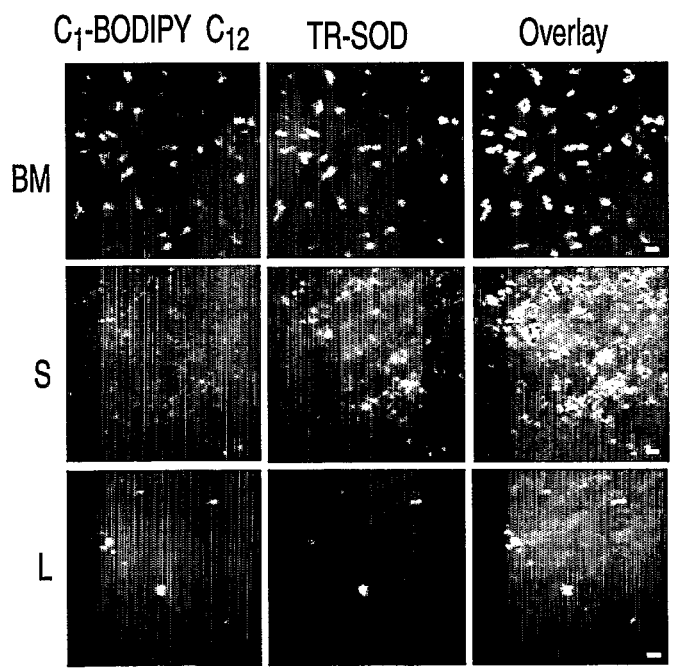

Microscopic Observation of In Vivo Targeting of Bone Marrow Using Vesicular Nanoparticles The initial studies were designed to demonstrate that the carboxylic acid residue-containing vesicles functions as a nanoparticulate carrier as well as identify their microscopic localization in tissues. The carboxylic acid residue-containing vesicles which are comprised of dipalmitoylphosphatidylcholine (45.5 mol %), cholesterol (45.5 mol %) and a carboxylic acid group-containing lipid compound (compound of formula (2) in which $R^3$ represents —$CH_2CH_2$—, and $R^4$ represents hexadecyl; 9.0 mol %) and PEG-DSPE (0.6 mol %), double fluorescently labeled by encapsulating superoxide dismutase (SOD) conjugated by Texas Red (TR) sulfonyl chloride (TR-SOD) in inner aqueous phase and embedding 4,4-difluoro-5-methyl-4-bora-3a,4a-diaza-s-indacene-3-dodecanoic acid ($C_1$-BODIPY $C_{12}$) in bilayer membrane (FIG. 6A) were prepared according to the modified method described in Example 1. SOD was purchased from Wako Pure Chemical Industries, Ltd. (Osaka, Japan). $C_1$-BODIPY $C_{12}$ and TR sulfonyl chloride were purchased from Molecular Probes, Inc. (Eugene, Oreg.). Conjugation of TR sulfonyl chloride to SOD was performed according to previously reported procedure (Lefevre et al., Bioconjug. Chem., 7(4): 482-489, 1996), and purified TR-SOD was encapsulated in mixed lipids including 1 mol % of $C_1$-BODIPY $C_{12}$ to obtain the double fluorescently-labeled the carboxylic acid residue-containing vesicles with size of 247±22 nm in diameter. Labeled vesicles were i.v. injected into anesthetized Male New Zealand White rabbits (2.5 kg, lipids: 15 mg/kg b.wt.). At 6 h after injection, femoral bone marrow tissues, liver and spleen were taken, fixed in 10% formalin solution, and then sliced into sections. The sections were fixed on the glass slides with agar at 4° C. and examined with a confocal scanning microscope (Olympus IX-70). As shown in FIG. 6B, the bone marrow sections have fluorescence from both the TR-SOD and $C_1$-BODIPY $C_{12}$-labeling the carboxylic acid residue-containing vesicles. The fluorescence was locally concentrated, and larger fluorescent domain was 30 μm in size along the long axis. Fluorescent distribution in red pulp of spleen was dense, whereas it was sparse in liver. An important finding from this observation is that the fluorescence from membrane probes and encapsulated probes are co-localized in bone marrow. These images clearly indicate that the carboxylic acid residue-containing vesicles functions as a nanoparticle-carrier to deliver the encapsulated agents to bone marrow tissues.

Transmission electron microscopic (TEM) observation was performed to observe the bone marrow tissues at a higher magnification. The carboxylic acid residue-containing vesicles which are comprised of dipalmitoylphosphatidylcholine (45.5 mol %), cholesterol (45.5 mol %) and a carboxylic acid group-containing lipid compound (compound of formula (2) in which $R^3$ represents —$CH_2CH_2$—, and $R^4$ represents hexadecyl; 9.0 mol %) and PEG-DSPE (0.6 mol %) were i.v. injected into anesthetized Male New Zealand White rabbits (2.5 kg). The rabbits received 15 mg/kg body weight of lipids. Control rabbits received no injection. Bone marrow was taken from the left femur of rabbits at 6 h after injection of vesicles, and fixed in 2.5% glutaraldehyde solution. The fixed bone marrow was then washed with 0.1 mol/L phosphate buffer, pH 7.4, and stained with 2% osumic acid solution at 4° C. for 2 h. The organs were first dehydrated stepwise with ethanol, and then polymerized using Quetol 812 at 60° C. for 28 h. The obtained samples were sliced into sections by using an Ultracut S microtome. The sliced samples were stained with 3% uranyl acetate solution for 20 minutes and then treated with Satoh's lead solution (lead acetate, lead nitrate, and lead citrate) in citrate for 5 minutes, washed, and dried. The sample was observed and a picture taken with a transmission electron microscope (TEM, H-7500, Hitachi, Tokyo, Japan). TEM observation clearly demonstrated the location of the carboxylic acid residue-containing vesicles in bone marrow (FIG. 7A, FIG. 7B). A massive number of vesicles were trapped in endosomes and lysosomes of macrophages, but no vesicles were observed in cytoplasm and cell nucleus (FIG. 7B). The diameter of these vesicles averaged 270 nm which was the original diameter of the intravenously administered carboxylic acid residue-containing vesicles. Several similar macrophages with vesicles in endosomes and lysosomes were observed, while no vesicles were observed in other types of cell such as granular leukocytes, erythroblasts, and endothelial cells in observed section. These microscopic localization studies demonstrate that macrophages are the cellular component responsible for clearance of vesicles from the circulation and their uptake by the bone marrow.

Example 10

Encapsulation of Drug into Carboxylic Acid Group-Containing Vesicles

Dipalmitoylphosphocholine (45.5 mol %), cholesterol (45.5 mol %), a carboxylic acid group-containing lipid compound (compound of formula (2) in which $R^3$ represents —$CH_2CH_2$—, and $R^4$ represents hexadecyl) (8.4 mol %), and PEG-DSPE (0.6 mol %) were dissolved in t-butanol, and the mixture was freeze-dried to prepare mixed lipid powder. The powder (0.8 g) was dispersed into 200 mM ammonium sulfate solution (20 mL) and stirred at 25° C. for 2 hours. The resultant mixture was placed into an EXTRUDER™ (available from Nichiyu Liposome, Japan) and sequentially passed through acetyl cellulose filters (available from Fuji Photo Film, Japan) having pore sizes of 3.0 μm, 0.8 μm, 0.65 μm, 0.45 μm, 0.30 μm, and 0.22 μm, respectively, under pressure (2 MPa) at 14° C., thereby preparing a vesicle dispersion. The unencapsulated ammonium sulfate was removed by ultracentrifugation ($3\times10^5$ g, 60 min each) and the vesicles were dispersed in saline solution to obtain carboxylic acid group-containing vesicles (lipid concentration: 40 mg/mL, mean diameter: 245±84 nm). An adriamycin solution (adriamycin concentration: 17.2 mM) which was prepared by dissolving a commercial adriamycin (62 mg) into physiological saline (6.2 mL) was added into the carboxylic acid group-containing vesicle dispersion (40 mg/mL, 11.3 mL, and then the mixture was allowed to stand at 55° C. for 10 minutes to encapsulate the adriamycin into inner aqueous phase of the carboxylic acid group-containing vesicles. The unencapsulated adriamycin was removed by ultracentrifugation ($3\times10^5$ g, 60 min). From the determination by an ultraviolet and visible spectropho-tometer (absorbance at 490 nm), the amount of free adriamycin collected in supernatant was calculated to be 3% of added adriamycin, indicating that 97% of added adriamycin was encapsulated into inner aqueous phase of vesicles. The precipitated vesicles were dispersed into physiological saline, and the vesicle dispersion was then passed through an acetyl cellulose membrane filter (pore size 0.45 μm, ADVANTEC) to obtain a desired dispersion of carboxylic acid group-containing vesicle-encapsulating adriamycin (volume: 13.2 mL).

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A bone marrow-directing drug delivery material comprising at least one fine particle having a diameter of 20 to 500 nm, wherein the fine particle further comprises:
   a first amphipathic compound having the following structure:

$MOOCR^3$—CO—$HNCH(COOR^4)CH_2CH_2COOR^4$, wherein M is a hydrogen atom or a monovalent cation, $R^3$ is —$CH_2CH_2$— and $R^4$ is a $C_{10}$-$C_{22}$ alkyl group; and
   a second amphipathic compound comprising 1,2-distearoyl-sn-glycero-3-phosphoethanolamine-N-[monomethoxy poly(ethylene glycol) (PEG-DSPE).

2. The material of claim 1, wherein the fine particle has a diameter of 100 to 500 nm.

3. The material of claim 1, wherein the particle is further defined as an aggregate of amphipathic molecules that form a vesicle.

4. The material of claim 1, wherein:
   the first amphipathic compound is present at 1 to 50 mol %, and wherein the second amphipathic compound is present at 0.5 to 4.8 mol %.

5. The material of claim 1, wherein at least one fine particle further comprises a drug bound to the at least one fine particle.

6. A method of preventing, treating, or diagnosing a disease of bone, cartilage, a joint, or bone marrow in a subject, comprising administering to the subject a pharmaceutically effective amount of the material of claim 1.

7. The method of claim 6, wherein the pharmaceutically effective amount of the material is 0.1 to 500 mg of the material per kg of body weight of the subject.

8. The method of claim 6, wherein the subject has a disease of bone marrow.

9. A method of preventing, treating, or diagnosing a joint disease in a subject, comprising administering to the subject a pharmaceutically effective amount of the material of claim 1.

10. The method of claim 9, wherein the pharmaceutically effective amount of the material is 0.1 to 500 mg of the material per kg of body weight of the subject.

11. The method of claim 1, wherein the subject is a human.

12. A kit comprising a predetermined amount of the material of claim 1 and a sealed container.

* * * * *